United States Patent [19]

Renger

[11] Patent Number: 5,557,967
[45] Date of Patent: Sep. 24, 1996

[54] THERMOPILE FLOW SENSOR

[75] Inventor: Herman L. Renger, Calabasas, Calif.

[73] Assignee: Pacesetter, Inc., Sylmar, Calif.

[21] Appl. No.: 393,955

[22] Filed: Feb. 24, 1995

[51] Int. Cl.$^6$ ........................................... G01F 1/68
[52] U.S. Cl. .................... 73/204.24; 73/204.11
[58] Field of Search .................. 73/14, 16, 22, 73/23, 24, 26, 204.24; 128/691, 692

[56] References Cited

U.S. PATENT DOCUMENTS

| | | | |
|---|---|---|---|
| 3,802,264 | 4/1974 | Poppendiek et al. | 73/204.24 |
| 4,890,489 | 1/1990 | Huijsing | 73/204.24 |
| 4,932,250 | 6/1990 | Assaf et al. | 73/204.24 |
| 5,174,299 | 12/1992 | Nelson | 128/692 |
| 5,351,551 | 10/1994 | Drubetsky et al. | 73/755 |

*Primary Examiner*—Richard Chilcot
*Assistant Examiner*—Max Noori
*Attorney, Agent, or Firm*—Harold C. Schloss

[57] ABSTRACT

A flow sensor adapted for placement along a pacing lead or other catheter comprises a thermopile formed on the outer surface of a tubular substrate. The thermopile comprises a plurality of interconnected conductors of an alternating metal type. Junctions between conductors of the thermopile are alternately located near the longitudinal ends of the flow sensor, so that a voltage generated by the thermopile indicates the difference in temperature between the ends of the flow sensor. To measure blood flow with the flow sensor, an alternating current is induced through the thermopile to heat the flow sensor in a generally symmetrical manner. A voltage generated by the thermopile is then measured to obtain a sample of the magnitude and direction of the velocity of blood flow.

9 Claims, 5 Drawing Sheets

U.S. Patent   Sep. 24, 1996   Sheet 1 of 5   5,557,967
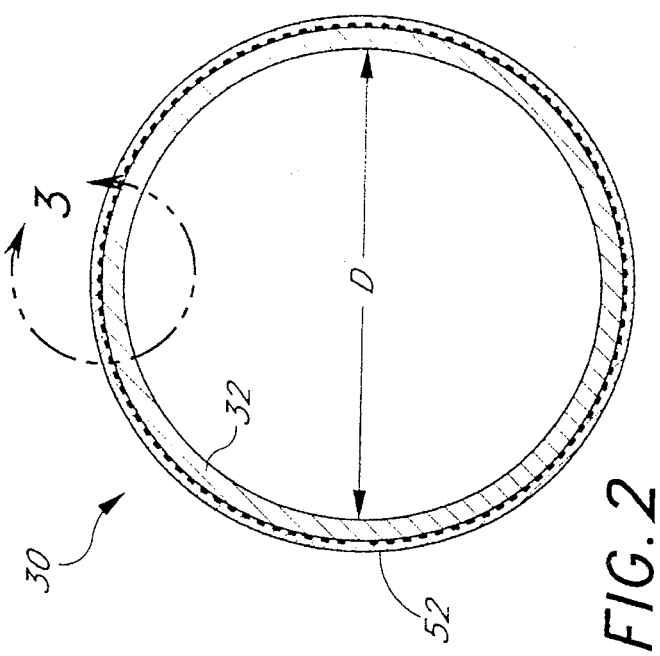
FIG. 2
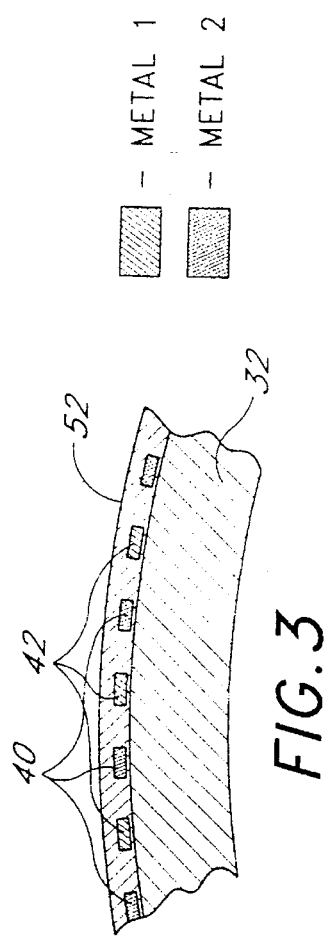
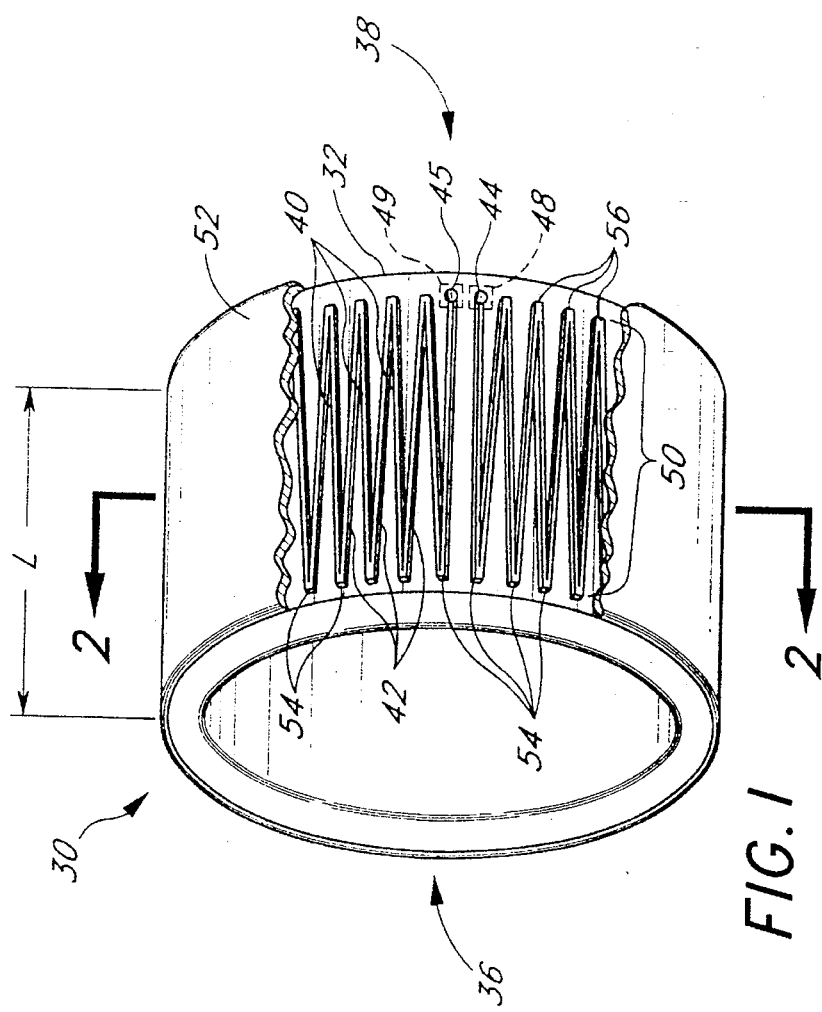
FIG. 3
FIG. 1

THERMOPILE FLOW SENSOR

FIELD OF THE INVENTION

This invention relates to sensors for measuring the flow of a fluid. In particular, this invention relates to a flow sensor for measuring the magnitude and direction of blood flow through a blood vessel.

BACKGROUND OF THE INVENTION

Cardiac pacing involves the electrical stimulation of the heart in order to control the timing of the contractions of the heart. Electrical stimuli in the form of pulses are generated by a battery-powered pacemaker and applied to the tissue of the heart using a pacing lead. The pacing lead may additionally be used to sense intrinsic electrical activity within the heart. The sensed electrical activity may be used by the pacemaker to control the timing of pulses that are applied to the heart, or may be used to select a particular pattern or method for pacing the heart.

Since the response of the heart to a particular pacing stimulus will typically vary from individual to individual, and may further change for a given individual with changing conditions, it is desirable to have an internally implantable device which measures the performance of the heart and supplies the measurement to the pacemaker. The measurements of cardiac performance can then be used by the pacemaker to adaptively adjust the pacing stimulus. Measurements of cardiac performance can also be communicated to a physician using telemetry techniques, and the physician can use the measurements to detect various abnormalities.

One method of measuring cardiac performance involves using an internally implanted flow sensor to measure the velocity of blood flow through a blood vessel. The sensed blood flow velocity is communicated to the pacemaker over wires that connect the flow sensor to the pacemaker. The sensed blood flood velocity may be used to estimate cardiac output, which is the volume of blood pumped by the heart per unit time. The sensed blood flow velocity may further be used to detect abnormal blood flow patterns, which may be caused, for example, by an improperly functioning heart valve.

Flow sensors can also be used with implantable defibrillators to detect or verify the absence of a heart beat. The defibrillator may then apply a shock to the heart to restart the heart.

As is known in the art, a thermocouple in conjunction with a heat source may be used to measure blood flow velocity. A thermocouple is a temperature sensor comprised of two dissimilar metals that are joined together to form a junction. A thermocouple may be formed, for example, by joining two wires of different metals together at one end. The junction between the wires may be placed at a measurement point while the opposite (i.e., unconnected) ends of the wires are held at a reference temperature. A voltage produced by the thermocouple across the unconnected ends of the of wires will then indicate the difference between the reference temperature and the temperature at the measurement point, and may thus be used to determine the temperature at the measurement point.

U.S. Pat. No. 5,174,299 to Nelson ("the Nelson Patent") discloses a flow sensor that uses a thermocouple to measure the velocity of blood flow. The flow sensor is adapted for placement along a pacing lead. The flow sensor comprises three metal tubes that are joined together from end to end to form two junctions, with the center tube composed of a different metal than the outer tubes. Wires connected to the junctions convey a voltage to the pacemaker that indicates a temperature difference between the two junctions. A heater provided proximate to the "upstream" junction is used to heat the upstream junction. A temperature difference between the two junctions is then monitored by the pacemaker to determine the rate at which heat is carried away from the upstream junction by the flow of blood.

The thermocouple-based flow sensor disclosed in the Nelson patent has a number of limitations. For example, the flow sensor does not detect the direction in which heat is carried away from the upstream junction, and thus effectively treats negative flow (i.e., flow in the reverse direction) and cross flow (i.e., side-to-side flow relative to the flow sensor) as positive flow. The treatment of negative flow as positive flow becomes a problem, for example, when a patient has a valve disorder that causes regurgitation (i.e., reverse flow) of blood through the valve as the heart muscle contracts. Since the flow sensor detects this reverse flow as positive flow, the pacemaker fails to detect the valve disorder. Moreover, the pacemaker counts the reverse flow as positive flow in measuring cardiac output, producing an inaccurate performance measurement. The treatment of cross flow as positive flow becomes a problem, for example, when cross flows occur in the region of the flow sensor as the result of side-to-side movement of the pacing lead. Such movement of the lead can occur as the result of the contractions of the heart. Failure to exclude cross flows from the flow measurement decreases the accuracy of the measurement of cardiac output.

The flow sensor disclosed in the Nelson patent further does not produce a zero-based voltage output (i.e., an output voltage of zero when the flow velocity is zero). This complicates accurate detection of very low and zero flow velocities. The flow sensor is thus not well suited for defibrillator applications, wherein detection of low flow rates is critical.

The flow sensor disclosed in the Nelson patent further requires the passage of two separate pairs of conductors through the lead between the flow sensor and the pacemaker or defibrillator. The first conductor pair carries the voltage generated by the thermocouple to the pacemaker. The second conductor pair carries a heating current from the pacemaker to the heater. The need for two separate conductor pairs affects the complexity of the lead, and affects the number of connectors that must be provided on the housing of the pacemaker. A need thus exists in the art to provide a thermocouple-based flow sensor that discriminates between forward and reverse flow, that is insensitive to cross flows, that accurately detects very low and zero flow velocities, and that requires the passage of only one pair of conductors between the flow sensor and the pacemaker or defibrillator.

SUMMARY OF THE INVENTION

The present invention comprises a flow sensor that uses a thermopile comprised of a plurality of series-connected thermocouples. Such thermocouples are formed from conductors of dissimilar metals that are joined together at junctions. The thermopile is utilized on a time-shared basis as both a heater for heating the flow sensor and a temperature sensor for sensing a temperature difference between the longitudinal ends of the flow sensor.

In a preferred embodiment, the thermopile extends circumferentially around the outer surface of a tubular substrate in a zigzag pattern. A plurality of conductors of an alternating metal type formed on the outer surface of the substrate extend substantially from one end to the opposite end of the tubular substrate. The conductors are connected end-to-end to one another at junctions to form a continuous electrical path between terminals of the thermopile. Due to the arrangement of the conductors, the junctions of the thermopile (which are formed by the interconnection of conductors of different metals) are alternately located at opposite ends of the tubular substrate so that a voltage is generated between the terminals of the thermopile whenever there is a difference in temperature between the two ends of the flow sensor. The terminals include respective pads to permit electrical connection of the flow sensor to a pacemaker, implantable defibrillator, or other device. A thin protective coating on the outer surface of the flow sensor covers the tubular substrate and the thermopile and serves as a medium for the transfer of heat between the thermopile and blood that flows past the outer surface of the flow sensor.

Samples of blood flow velocity may be periodically taken by heating the flow sensor and then measuring a voltage generated by the thermopile. The flow sensor is heated by passing a heating current through the thermopile. The direction of the heating current is periodically reversed during the heating process to neutralize the Peltier effect, which is a heating effect that causes uneven heating of the junctions when a dc current is passed through the thermopile. The flow sensor is thereby heated in a generally symmetrical manner, with opposite ends of the flow sensor heated approximately equally.

When no blood flows past the heated flow sensor, the ends of the flow sensor remain at the same temperature relative to one another, and the flow sensor (i.e., the thermopile) outputs a voltage of zero. When blood flows past the heated flow sensor, a temperature difference develops between the ends of the flow sensor, since a greater amount of heat is transferred into the blood stream at the upstream end of the heated sensor than the downstream end. The thermopile generates a voltage that is proportional to this temperature difference. The polarity of the temperature difference, and thus the polarity of the voltage generated by the thermopile, indicates the direction of blood flow. The magnitude of the temperature difference, and thus the magnitude of the voltage, indicates the speed of the blood flow. The voltage generated by the flow sensor varies approximately linearly with the flow velocity over an expected range of flow velocities.

Since the thermopile is used on a time-shared basis as both a heater for heating the flow sensor and a sensor for sensing a temperature difference, only two wires need to be passed between the flow sensor and the pacemaker or defibrillator. The number of connections to the pacemaker or defibrillator is thus reduced over prior art designs that require four wires. The complexity of the lead on which the flow sensor is mounted is also reduced.

The capability of the flow sensor to discriminate between forward and reverse flow enables the flow sensor to detect abnormal flow patterns, and ensures that reverse blood flow will not be treated as forward blood flow when measuring cardiac output. Further, the zero-based, approximately linear output of the flow sensor facilitates detection of low and zero flow velocities, as is particularly desirable in defibrillation applications.

As a result of a generally symmetrical construction of the flow sensor, and the method of the present invention of heating the flow sensor in a generally symmetrical manner, the flow sensor is highly insensitive to cross flows over prior art designs. This ensures that cross flows will not significantly affect the blood flow measurement if the flow sensor moves from side-to-side within the blood vessel.

Other features and advantages of the present invention will be apparent from the detailed description which follows.

BRIEF DESCRIPTION OF THE DRAWINGS

FIG. 1 is a perspective view of a flow sensor in accordance with the present invention, with a protective coating layer cut away to reveal the construction of the flow sensor.

FIG. 2 is a cross sectional view taken along the line 2—2 of FIG. 1.

FIG. 3 is an enlarged view taken from the line 3—3 of FIG. 2, showing how conductors of the flow sensor alternate in metal type.

DETAILED DESCRIPTION OF THE PREFERRED EMBODIMENTS

Figure 4:
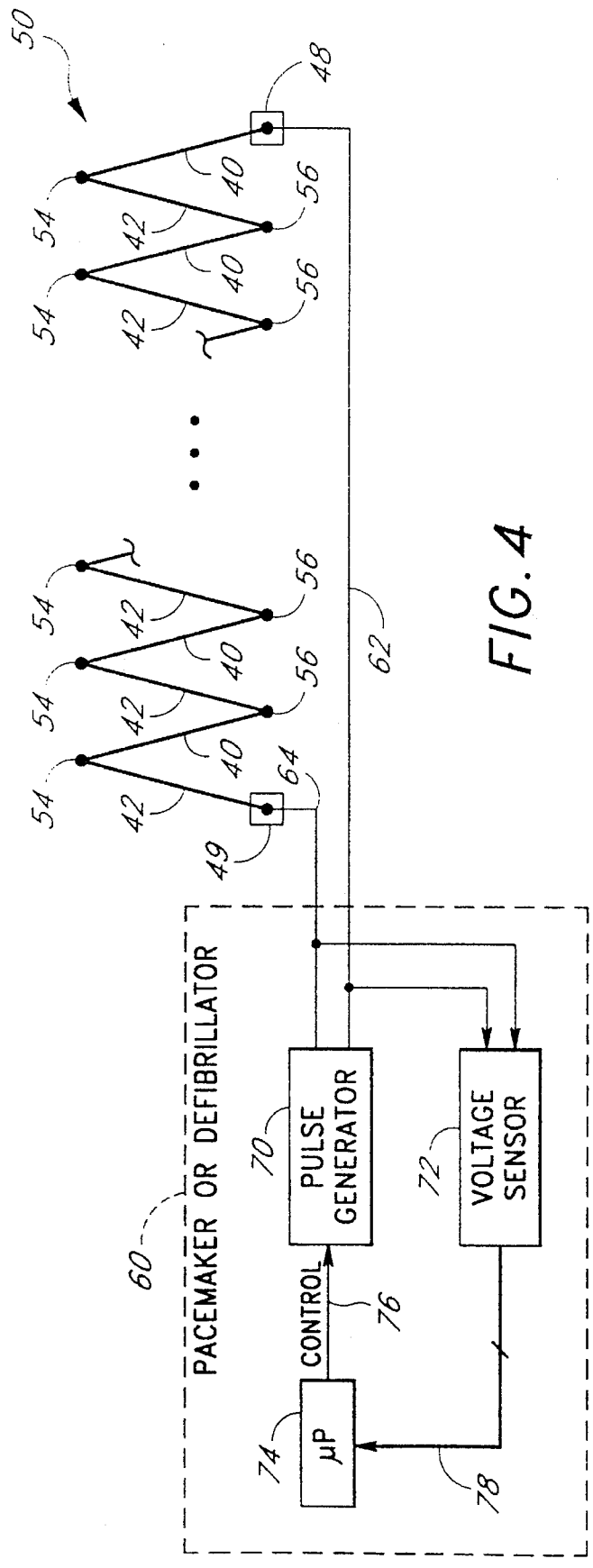
FIG. 4 is a schematic diagram of the circuit of the flow sensor, with the circuit connected to a pulse generator and a voltage sensor of a pacemaker or defibrillator.

As illustrated in FIGS. 1–3, a flow sensor 30 comprises a tubular substrate 32 having a first end 36 and a second end 38. The substrate 32 is preferably composed of a ceramic material such as aluminum oxide ($Al_2O_3$). The inner diameter D of the tubular substrate 32 is preferably approximately two to three millimeters, allowing the flow sensor 30 to be mounted along the outside of a catheter such as a pacing lead or a defibrillation lead. The longitudinal length L of the substrate 32 (and flow sensor 30) is preferably less than one millimeter.

Formed on the outer surface of the substrate 32 is a first set of conductors 40 of a first metal type. Also formed on the outer surface of the substrate 32 is a second set of conductors 42 of a second metal type that differs from the first metal type. Each conductor 40, 42 extends substantially from one end 36 to the other end 38 of the flow sensor 30. The conductors 40 and 42 are preferably thin film traces that are disposed on the substrate 32 using thin film deposition techniques that are known in the art. Alternatively, the conductors 40 and 42 may be wires, such as one mil (0.001 inch diameter) wires.

The conductors 40 and 42 are arranged in an alternating manner, and are connected end-to-end to one another to form a continuous electrical path that extends circumferentially around the outer surface of the substrate 32 in a generally uniform, zigzag pattern. Each conductor 40 and adjacent conductor 42 to which it is connected forms a thermocouple. The thermocouples are connected in series to form a thermopile 50. Junctions 54 and 56 of the thermopile 50 (between conductors 40, 42 of dissimilar metals) are alternately positioned proximate to opposite longitudinal ends 36, 38 of the flow sensor 30.

Vias 44 and 45 extend through the substrate 32 to pads 48 and 49 that are located on the inner surface of the substrate 32 (pads shown in dashed lines in FIG. 1). The conductors 40 and 42 at opposite ends of the thermopile 50 are conductively connected to the pads 48 and 49. The pads 48 and 49 permit the thermopile 50 to be conductively connected to a pacemaker, defibrillator, or other device (as illustrated in FIG. 4).

In the preferred embodiment, approximately 100 one-half-millimeter-long conductors 40, 42 are used, resulting in a thermopile 50 that consists of fifty thermocouples. However, as will be recognized by those skilled in the art, the number and length of the conductors 40, 42 can be varied significantly. As will further be recognized, the thickness of the conductors 40 and 42 may be varied to produce an impedance for the thermopile 50 that is suitable for the circuitry to which the thermopile 50 is connected. In the preferred embodiment, the thermopile 50 has an impedance of about 9000 Ω.

A thin, protective coating 52 is provided over the outer surface of substrate 32, covering the conductors 40, 42. When the flow sensor 30 is implanted within a blood vessel, the protective coating 52 serves to insulate the conductors 40, 42 from the blood which flows along the outer surface of the flow sensor 30. The protective coating 52 is preferably an electrically nonconductive, biocompatible material that is suitable for transferring heat between conductors 40, 42 and the bloodstream. Examples of materials that are suitable for this purpose include glass, diamond, quartz, and pyrolytically deposited carbon. Pyrolytically deposited carbon has the advantageous property of being anisotropic, meaning that it conducts heat in one direction better than other directions. It is contemplated that pyrolytically deposited carbon can be deposited on the outer surface of the substrate 32 such that it conducts heat in a radial direction (i.e., between the conductors 40, 42 and the blood stream) better than it conducts heat in a longitudinal or tangential direction. As will be recognized by those skilled in the art, heat transfer in this manner will enhance the operation of the flow sensor 30.

Referring to FIG. 1, when the junctions 54 are greater in temperature than the junctions 56, the thermopile 50 will generate a voltage that is proportional to the temperature difference. When the junctions 54 are lower in temperature than the junctions 56, the thermopile 50 will generate a voltage that is proportional to the temperature difference, and which is opposite in polarity from the voltage generated when the junctions 54 are warmer than the junctions 56. The thermopile 50 thus acts as a temperature sensor for sensing a temperature difference between the ends 36, 38 of the flow sensor 30. Assuming that all of the junctions 54 are at one temperature and all of the junctions 56 are at a second temperature, the voltage generated by the thermopile 50 will be equal to the voltage generated by each thermocouple multiplied by the number of thermocouples. The voltage generated by each thermocouple is commonly referred to as the Seebeck voltage (or Seebeck EMF).

FIG. 4 illustrates the electrical interconnection of the thermocouple 50 to internal circuitry of a pacemaker or defibrillator 60. The pads 48 and 49 are connected to the pacemaker or defibrillator 60 by conductors 62 and 64 respectively. The conductors 62 and 64 are preferably formed within an insulating material of a lead (FIG. 7) on which the flow sensor 30 is mounted. Internal to the pacemaker or defibrillator 60, the conductors 62 and 64 are connected to a pulse generator 70 and a voltage sensor 72. The pulse generator 70 is connected to a microprocessor (μP) 74 by a control line 76. The voltage sensor 72 is connected to the microprocessor 76 by a bus 78.

In order to induce a temperature differential across the flow sensor 30 that is indicative of the velocity and direction of blood flow, the flow sensor 30 is initially heated in a symmetrical and generally uniform manner. Heating is accomplished by passing a current through the thermopile 50. The current is induced by the pulse generator 70, which applies a series of voltage pulses to the thermopile 50 via the conductors 62 and 64. Once the flow sensor 30 has been sufficiently heated, the pulse generator 70 is switched to a high impedance state, and the voltage sensor 72 measures the voltage across the thermopile 50. This voltage represents the temperature difference between the ends 36, 38 of the flow sensor 30 that results from the flow of blood. The voltage sensor 72 then provides one or more data values to the microprocessor 74 on the bus 78 that indicate the measured voltage. This process of heating the flow sensor 30 and then measuring the voltage is repeated periodically to obtain samples of the blood flow velocity at various stages of the cycle of the heart.

To understand the preferred method for heating the flow sensor 30 in a symmetrical fashion, it is important to understand how the thermopile 50 reacts when a dc current is passed therethrough. When a dc current is passed through the thermopile 50 in one direction, one set of junctions 54 or 56 (depending upon the types of metals used for the conductors 40 and 42) increases in temperature while the other set of junctions 56 or 54 decreases in temperature. This warming/cooling effect is commonly known as the Peltier effect, and produces the undesirable result of inducing a temperature difference between the ends 36, 38 of the flow sensor 30. The warming/cooling phenomenon of the Peltier effect is reversed when the direction of current flow through the thermopile 50 is reversed. Thus, for example, if the junctions 54 warm and the junctions 56 cool when a positive current is passed through the thermopile 50 from the pad 48 to the pad 49, the junctions 54 will cool and the junctions 56 will warm if the direction of current flow is reversed.

In the preferred embodiments, the temperature difference caused by the Peltier effect is neutralized by periodically alternating the direction of the heating current that is passed through the thermopile 50 so that the heating and cooling of the junctions 54 and 56 is symmetrical (i.e., the junctions 54 are heated and cooled by the same amount as the junctions 56). Heating of the flow sensor 30 results from the alternating current primarily as a consequence of power dissipation within the conductors 40 and 42, which occurs in accordance with the equation $P=I^2R$ (where P=power, I=current, and R=the resistance of the thermopile 50).

Figure 5:
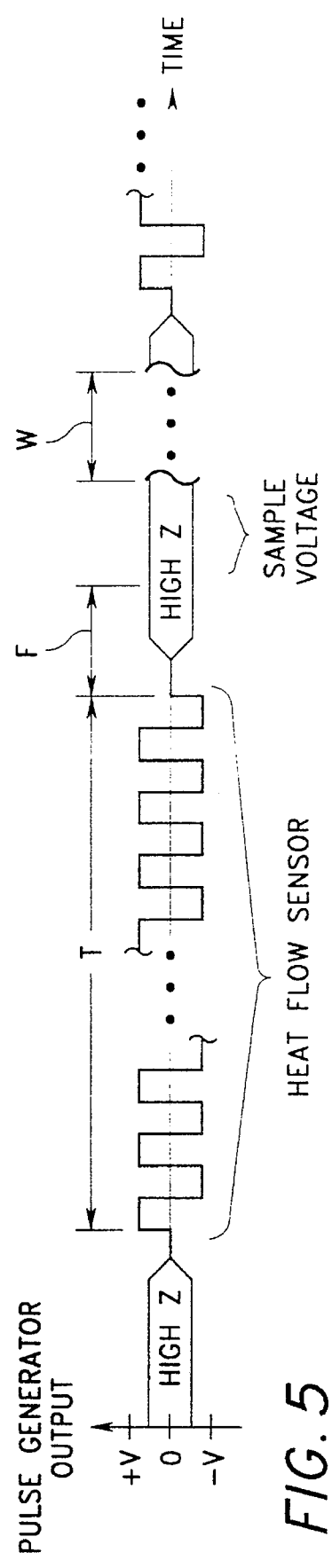
FIG. 5 is a timing diagram illustrating a blood flow measurement cycle.

FIG. 5 further illustrates the process of heating the flow sensor 30 and measuring the voltage generated by the thermopile 50. During a heating period T, the pulse generator 70 (FIG. 4) generates a continuous series of voltage pulses of amplitude V that are applied to the thermopile 50. The pulses may alternatively be applied to the thermopile 50 as a sequence of pulse bursts. The pulses alternate in polarity, so that the flow sensor 30 is heated in a symmetrical fashion. In the preferred embodiment, the heating period T is on the order of ten milliseconds, and the amplitude V of the pulses is in the range of 3 to 6 volts. The power dissipated during the heating period T will typically be about one milliwatt or less, and will typically produce a temperature increase of about one degree fahrenheit or less throughout the flow sensor 30. Heating can be increased or decreased by adjusting the duration of the heating period T, and/or by adjusting the amplitude of the pulses. The pulse waveform preferably has a frequency in the range of 1 KHz to 10 KHz. Frequencies of less than 1 KHz tend to produce asymmetrical heating of the flow sensor 30 as the result of the Peltier effect.

At the end of the heating period T, the pulse generator 70 is switched to a high impedance (high Z) state to allow the voltage sensor 72 to measure a dc voltage generated by the thermopile 50. This dc voltage is proportional to the temperature difference between the ends 36, 38 of the flow sensor 30 caused by the flow of blood. The pacemaker or defibrillator 60 may wait for a flow interval F (typically in the range one millisecond) before sampling the dc voltage, to allow the temperature difference between the ends 36 and 38 to peak. The dc voltage may alternatively be sampled immediately after the heating period T, since a temperature difference will develop across the flow sensor 30 during the heating period T if blood is flowing. The voltage sensor 72 provides a digital representation of the sensed voltage to the microprocessor 74 on the bus 78.

Figure 6:
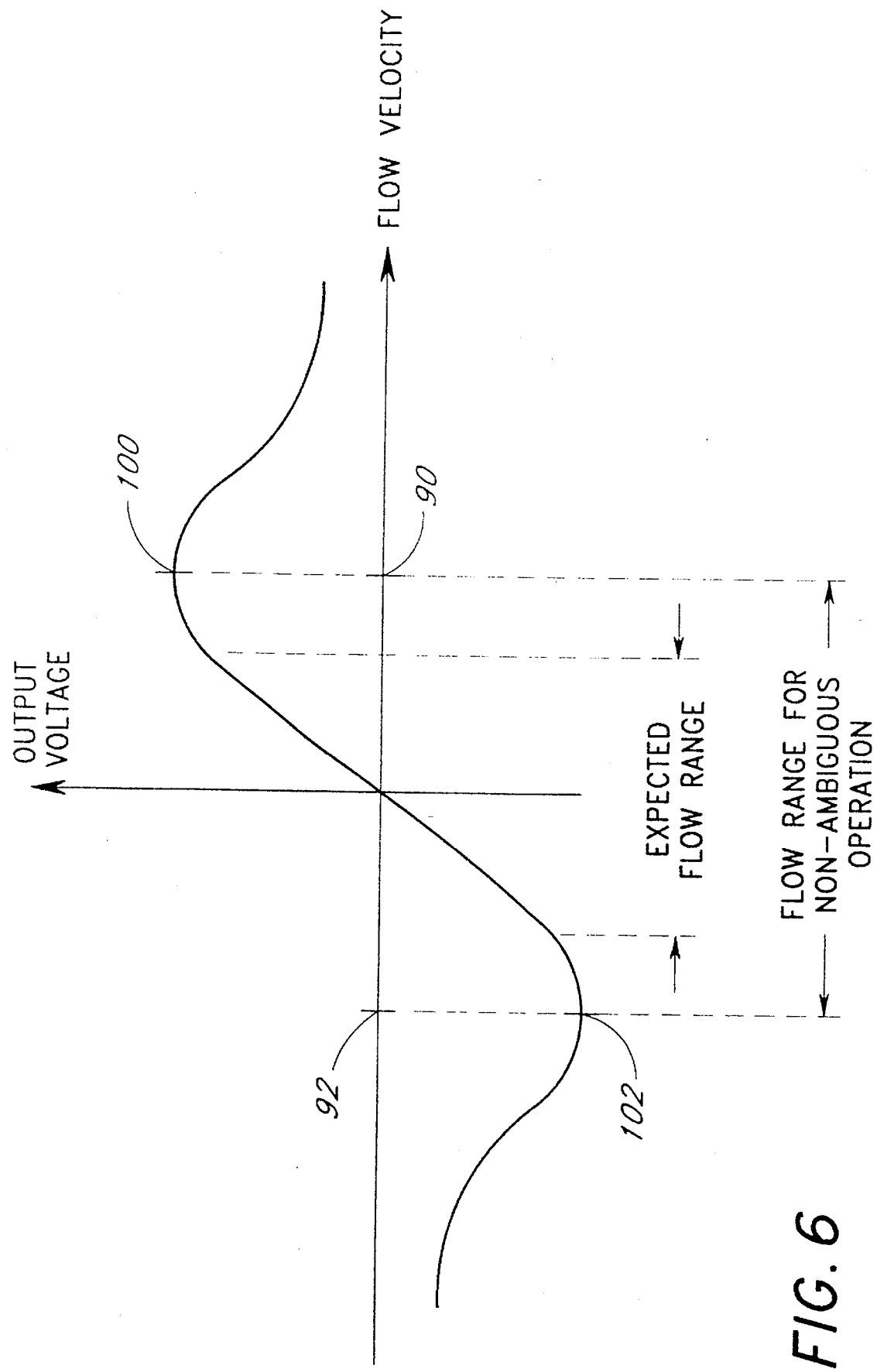
FIG. 6 is a graph showing the relationship between blood flow velocity and a dc voltage generated by the flow sensor.

The general form of the response curve for the flow sensor 30 is illustrated by FIG. 6. This curve represents the dc voltage generated by the thermopile 50 for different levels of blood flow velocity once the flow sensor 30 has been heated in a generally symmetrical manner.

As indicated by FIG. 6, the voltage will be zero (indicating a temperature difference of zero) if the blood flow is zero, since the junctions 54 and 56 have been heated by the same amount (during the heating period T), and are affected equally by the absence of blood flow. If blood flows in either direction, the upstream end of the flow sensor 30 will be cooled to a greater degree than the downstream end, since the blood will be warmed as it passes along the outer surface of the flow sensor 30 from one end to the other. A temperature difference between the ends 36, 38 of the flow sensor 30 will thus be induced, causing a voltage to be generated by the thermopile 50. Since the polarity of the voltage generated by the thermopile 50 depends upon which set of junctions 54 or 56 is warmer than the other, the polarity of the voltage indicates the direction of blood flow. The flow sensor 30 can thus be used to sense the direction of blood flow.

Within a range of blood flow bounded by flow velocities 90 and 92 (corresponding to peaks 100 and 102 respectively in the curve), increases in the rate of blood flow produce larger temperature differences between the ends 36, 38 of the flow sensor 30, producing voltages of greater magnitude. As the magnitude of blood flow velocity increases beyond the flow velocities 90 and 92, the temperature difference caused by the blood flow begins to decrease, producing voltages of lower magnitude. The flow velocities 90 and 92 thus represent the maximum forward and reverse flow velocities for non-ambiguous operation of the flow sensor 30. Provided that blood flow remains within the range of non-ambiguous operation, the voltage generated by the flow sensor 30 uniquely corresponds to a particular velocity of flow. The maximum forward and reverse flow velocities 90 and 92 for non-ambiguous operation are a function of the longitudinal length L (FIG. 1) of the flow sensor 30. The flow sensor 30 is preferably designed so that the expected range of blood flow velocity falls well within the range of non-ambiguous operation.

As illustrated by FIG. 6, output of the flow sensor 30 is approximately linear through zero blood flow. This characteristic of the flow sensor 30 facilitates the detection of low blood flow levels in comparison with prior art designs. The ability to detect low levels of blood flow is useful, for example, in defibrillator applications, wherein it is important to have the ability to discriminate between low rates of blood flow and zero blood flow.

Referring again to FIG. 5, once a sample of the blood flow velocity has been obtained, the microprocessor 74 waits for a time period W before initiating the next heating/sensing cycle. The time period W may vary from several milliseconds or less to several days or more, depending upon the particular application for which the flow sensor 30 is used. For example, in defibrillator applications, wherein the flow sensor 30 is used primarily to determine whether the heart has stopped, a flow sample (or several consecutive flow samples) may be taken every minute or so, or may be taken only when other indications suggest that the heart has stopped. For pacing applications, wherein the flow sensor 30 is used to measure cardiac output, or is used to detect abnormal blood flow patterns, a series of consecutive flow samples may be timed to coincide with stimulation and subsequent contraction of the right ventricle, and the process may be repeated every day or so.

The above-described flow sensor 30 and associated method provide numerous advantages over prior art thermocouple-based flow sensors. For example, the timed-shared use of the thermopile 50 as both a heater and a temperature sensor eliminates the need for a separate heater, and reduces the number conductors that must be passed through the lead and connected to the pacemaker or defibrillator 60. Further, the ability to detect the direction of blood flow permits detection of abnormal regurgitation of blood through one or more valves of the heart, and ensures that negative blood flow will not be treated as positive blood flow in measuring cardiac output.

The flow sensor 30 also achieves a high degree of insensitivity to cross flows in comparison with prior art designs. Since the flow sensor 30 is heated in a generally symmetrical manner and has a generally symmetrical construction, a cross flow will effect both ends 36 and 38 of the flow sensor 30 approximately equally, and thus will not create a temperature difference between the ends 36 and 38. Cross flows thus will not significantly affect the blood flow measurement if the flow sensor moves from side-to-side within the blood vessel.

Figure 7:
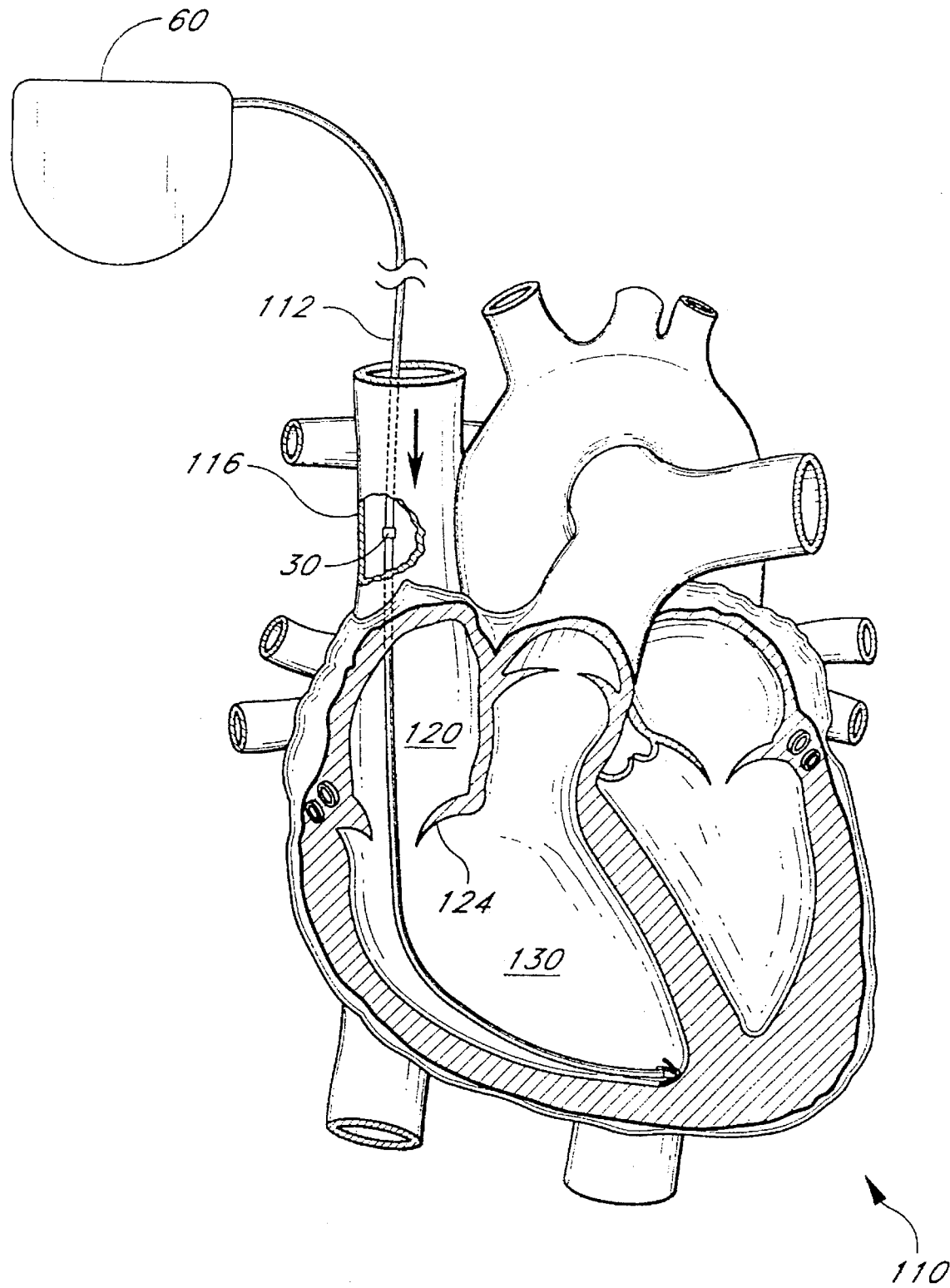
FIG. 7 is a perspective view in partial cross section, showing the flow sensor mounted on a pacing lead that is implanted within a human heart.

FIG. 7 illustrates how the flow sensor 30 may be positioned relative to a human heart 110 to sense cardiac output and to detect abnormal regurgitation of blood. The flow sensor 30 is shown mounted on a pacing lead 112 and positioned within the superior vena cava 116. The lead 112 is shown as extending through the right atrium 120 and tricuspid valve 124, and into the right ventricle 130. Two conductors 62 and 64 (FIG. 4) extend proximally from the flow sensor 30 through the lead 112 to conductively connect the flow sensor 30 to a pacemaker 60.

During normal operation of the heart 110, blood flows through the superior vena cava 116 in the direction of the arrow in FIG. 7. The rate of blood flow, which is directly proportional to the velocity of flow, is an indication of cardiac output, and may be used by the pacemaker 60 to adjust the timing of stimulation pulses applied to the heart 110.

When the right atrium 120 contracts, some negative blood flow (i.e., flow opposite the direction of the arrow) will normally occur through the superior vena cava 116. The prior art thermocouple-based flow sensor described above detects this negative blood flow as positive blood flow, reducing the accuracy of the cardiac output measurement. Since the flow sensor 30 detects the direction of blood flow, the pacemaker 60 can ignore this negative blood flow, and thus generate a more accurate measurement of cardiac output.

When the right ventricle 130 contracts, little or no negative blood flow normally occurs in the superior vena cava 116. If the tricuspid valve 124 is not functioning properly, however, blood may be regurgitated through tricuspid valve 124 during the ventricular contraction, causing negative flow through the superior vena cava 116. Such regurgitation of blood may occur, for example, if the tricuspid valve 124 is damaged during implantation of the lead 112, or if the lead 112 is improperly positioned within the heart 110. The negative blood flow caused by the regurgitation may be detected, for example, by sampling the blood flow during or just after stimulation of the right ventricle 130. The pacemaker 60 may then alert a doctor or patient of the abnormality using telemetry techniques that are well known in the art.

Figure 8:
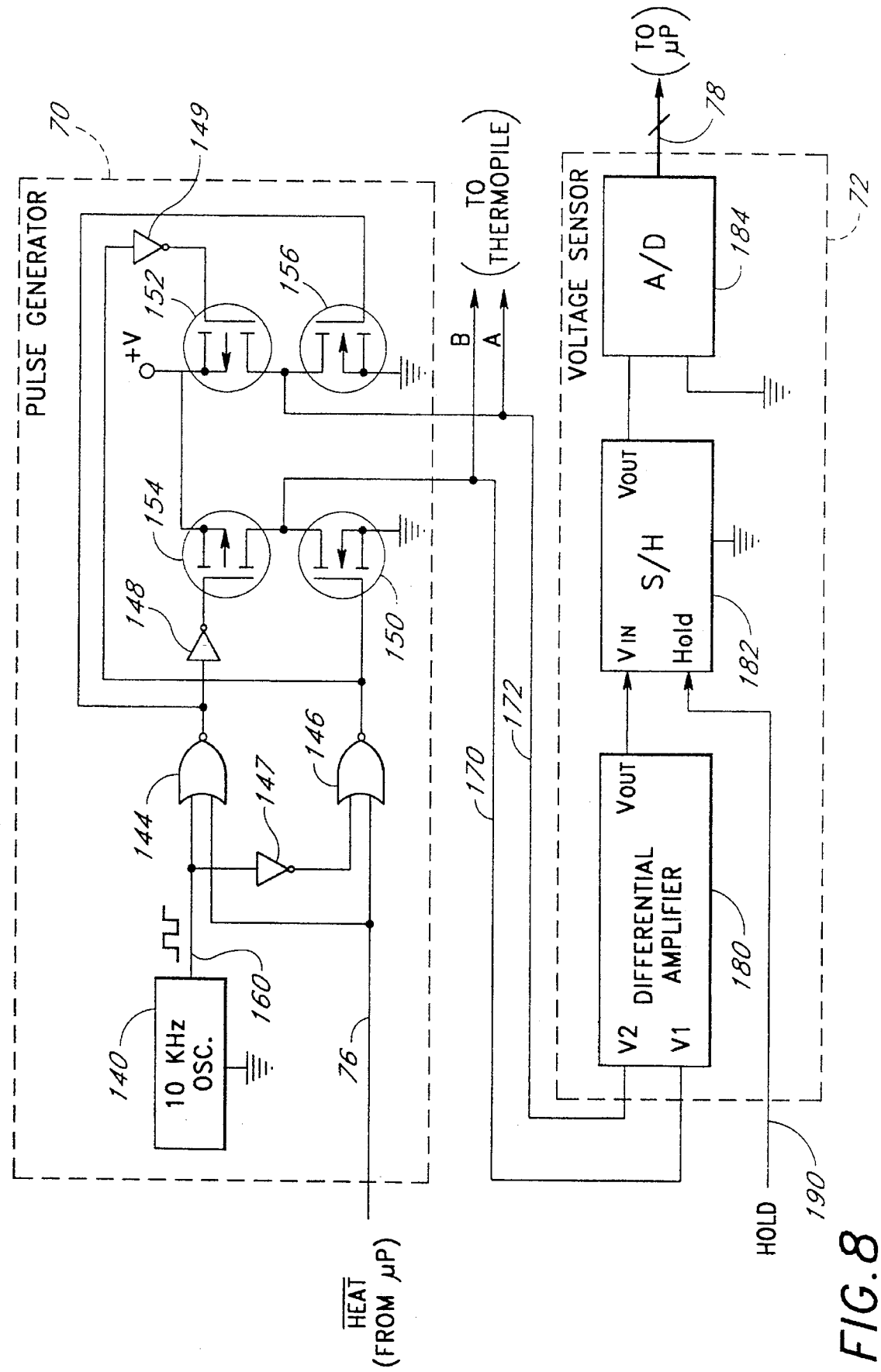
FIG. 8 is a circuit diagram for the pulse generator and voltage sensor of FIG. 4.

FIG. 8 illustrates the circuitry of the pulse generator 70 and the voltage sensor 72 of FIG. 4. The pulse generator comprises a 10 KHz oscillator (OSC.) 40, two NOR gates 144 and 146, three inverters 147, 148 and 149, two N-channel enhancement mode MOSFETs 150 and 156, and two P-channel enhancement mode MOSFETs 152 and 154. As will be recognized by those skilled in the art, other types of switching transistors can be used in place of the MOSFETs 150, 152, 154 and 156. The output of the oscillator 140 is connected by a line 160 to a first input of the NOR gate 144 and to the input of the inverter 147. The output of the inverter 147 is connected to a first input of the NOR gate 146. A $\overline{\text{HEAT}}$ signal line 76 (also shown in FIG. 4 as a CONTROL line 76) is connected to the second input of the NOR gate 144, and to the second input of the NOR gate 146. The output of the NOR gate 144 is connected to the input of the inverter 148, and is also connected to the gate of the MOSFET 156. The output of the inverter 148 is connected to the gate of the MOSFET 154. The output of the NOR gate 146 is connected to the gate of the MOSFET 150, and is also connected to the input of the inverter 149. The output of the inverter 149 is connected to the gate of the MOSFET 152. The sources of the MOSFETs 152 and 154 are connected to a positive voltage source +V, corresponding to the pulse amplitude V shown in FIG. 5. The sources of the MOSFETs 150 and 156 are connected to ground. The drains of the MOSFETs 150 and 154 are connected to one another, and are also connected to a line 170, which in turn, is connected to one end 62 of the thermopile 50 (FIGS. 1 and 4). The drains of the MOSFETs 152 and 156 are similarly tied together, and are connected to a line 172, which in turn, is connected to the other end 64 of the thermopile 50.

The voltage sensor 72 comprises a differential amplifier 180, a sample and hold (S/H) circuit 182, and an analog-to-digital (A/D) converter 184. The lines 170 and 172 are connected to the signal inputs (V1 and V2) of the differential amplifier 180. The output (VOUT) of the differential amplifier 180 is connected to the voltage input (VIN) of the sample and hold circuit 182. The Hold input of the sample and hold circuit 182 is connected to a HOLD signal line 190, which may be provided as an output line from the microprocessor 74 (FIG. 4). The output (VOUT) of the sample and hold circuit 182 is connected to the analog-to-digital converter 184. The analog-to-digital converter has a multi-bit output that is connected by the bus 78 (also shown in FIG. 4) to the microprocessor 74 (FIG. 4).

In operation, the microprocessor 74 (FIG. 4) controls the $\overline{\text{HEAT}}$ signal line 76 to switch between a heating mode, wherein a pulse signal is applied to the thermopile 50, and a non-heating mode, wherein the pulse generator 70 is in a high impedance state. When the $\overline{\text{HEAT}}$ signal line is high (inactive), the respective outputs of the NOR gates 144 and 146 are low, maintaining the MOSFETs 150, 152, 154 and 156 in a nonconductive or "OFF" state. The lines 170 and 172 are thereby isolated from the voltage source (+V) and ground, and the pulse generator is 70 maintained in a high impedance state.

When the $\overline{\text{HEAT}}$ signal line is low (active), the NOR gates 144 and 146 are effectively enabled, and the output of the oscillator 140 controls the states of the MOSFETs 150, 152, 154 and 156. When the output of the oscillator 140 becomes high, the outputs of the NOR gates 144 and 146 become low and high respectively, so that the respective gates of the MOSFETs 152 and 156 are low and the respective gates of the MOSFETs 150 and 154 are high. The MOSFETs 150 and 152 are thus placed in a conductive or "ON" state, and the MOSFETs 154 and 156 are turned OFF. The line 170 is thus switched to ground, and the line 172 is switched to +V volts. A voltage pulse of $V_{A-B}=+V$ volts is thus applied to the thermopile 50. When the output of the oscillator 140 becomes low, the outputs of the NOR gates 144 and 146 become high and low respectively, so that the respective gates of the MOSFETs 152 and 156 are high and the respective gates of the MOSFETs 150 and 154 are low. The MOSFETs 150 and 152 are thus placed in an OFF state, and the MOSFETs 154 and 156 are switched ON. The line 170 is thus switched to +V volts, and the line 172 is switched to ground. A voltage pulse of $V_{A-B}=-V$ volts is thus applied to the thermopile 50. A 10 KHz train of pulses of alternating polarity is thus applied to the thermopile 50.

When the pulse generator 70 is turned off (i.e., the $\overline{\text{HEAT}}$ line 76 is held high by the microprocessor 74), the differential amplifier 180 outputs a voltage that represents the voltage difference between the lines 170 and 172. Analog switches (not shown) controlled by the $\overline{\text{HEAT}}$ signal line 76 can be employed to isolate the differential amplifier 180 from the lines 170 and 172 when the pulse generator 70 is on. The sample and hold (S/H) circuit 182 samples and holds the voltage output of the differential amplifier 180 in response to a HOLD signal on the HOLD signal line 190 to produce a stable analog voltage at the input of the analog-to-digital (A/D) converter 184. The HOLD signal is preferably generated by the microprocessor 74 (FIG. 4), but may alternatively be derived from the $\overline{\text{HEAT}}$ signal. The analog-to-digital converter 184 outputs a digital value on the bus 78 that represents the voltage across the lines 170 and 172.

Referring to FIGS. 4, 5 and 8, in a typical blood flow measurement cycle the microprocessor 74 operates as follows. The microprocessor 74 drives the $\overline{\text{HEAT}}$ signal line 76 low for the heating period T (FIG. 5) to apply a 10 KHz train of pulses of alternating polarity to the flow sensor 30. After the heating period T, the microprocessor 74 waits for the flow interval F (FIG. 5), and then asserts the HOLD signal to stabilize the output of the analog-to-digital converter 184. The microprocessor 74 then reads the output of the analog-to-digital converter 184 to obtain a numerical representation of the voltage generated by the thermopile 50. The microprocessor 74 may then correlate this number to a specific flow velocity using a lookup table or equation that represents the response curve (FIG. 6) for the flow sensor 30.

While various embodiments of a flow sensor 30 and a method for sensing blood flow have been described, these embodiments have been presented by way of example only, and are not intended to limit the scope of the present invention. Further, while the present invention is described herein in the context of measuring blood flow, it will be apparent to those skilled in the art that the invention is also applicable to flow measurements of other types of fluids. Thus, the breadth and scope of the present invention should be defined only in accordance with the following claims and their equivalents.

What is claimed is:

1. A flow sensor, comprising:
   a series of interconnected thermocouples which form a series of junctions, said series of junctions comprising first and second sets of junctions, said first set of junctions spatially separated from said second set of junctions in a direction of flow to be sensed, wherein said series of interconnected thermocouples comprises means for heating said flow sensor when an alternating heating current is passed through said series of interconnected thermocouples, wherein said series of thermocouples is formed on a substrate, wherein junctions of said first set are proximate to a first end of said substrate and junctions of said second set are proximate to a second end of said substrate, and wherein said series of thermocouples is arranged on said substrate such that a polarity of a voltage generated by said series of thermocouples indicates a polarity of a temperature difference between said first and second ends.

2. A flow sensor according to claim 1, wherein junctions of said first set are proximate to one another, and wherein junctions of said second set are proximate to one another.

3. A flow sensor according to claim 1, wherein every other junction of said series of junctions is within said first set of junctions.

4. A flow sensor according to claim 1, wherein each junction of said first set is connected to a junction of said second set, and wherein each junction of said second set is connected to a junction of said first set.

5. A flow sensor according to claim 1, wherein said series of interconnected thermocouples is distributed along said substrate such that the flow sensor is heated in a generally uniform manner when said alternating heating current is passed through said series of thermocouples.

6. A flow sensor according to claim 1, wherein junctions in said series of junctions alternate between said first and second ends of said substrate.

7. A flow sensor according to claim 1, wherein said substrate is tubular.

8. A flow sensor according to claim 1, further comprising a protective coating on at least a portion of said substrate, said protective coating covering conductors of said series of thermocouples.

9. A flow sensor according to claim 8, wherein said protective coating is selected from a group consisting of glass, quartz, diamond, and pyrolytically deposited carbon.

* * * * *